(12) United States Patent
Matge et al.

(10) Patent No.: US 9,259,325 B2
(45) Date of Patent: *Feb. 16, 2016

(54) DYNAMIC INTERVERTEBRAL IMPLANT

(75) Inventors: Guy Matge, Mamer (LU); Jean-Jacques Martin, Bourg En Bresse (FR)

(73) Assignee: PARADIGM SPINE, LLC, New York, NY (US)

( * ) Notice: Subject to any disclaimer, the term of this patent is extended or adjusted under 35 U.S.C. 154(b) by 193 days.

This patent is subject to a terminal disclaimer.

(21) Appl. No.: 12/986,714

(22) Filed: Jan. 7, 2011

(65) Prior Publication Data

US 2011/0106256 A1 May 5, 2011

Related U.S. Application Data

(63) Continuation of application No. 10/506,219, filed as application No. PCT/FR03/00799 on Mar. 13, 2003, now Pat. No. 7,867,276.

(30) Foreign Application Priority Data

Mar. 15, 2002 (FR) ...................................... 02 03252

(51) Int. Cl.
  *A61F 2/44* (2006.01)
  *A61B 17/70* (2006.01)
  *A61B 17/86* (2006.01)
  *A61F 2/30* (2006.01)
  *A61F 2/28* (2006.01)

(52) U.S. Cl.
  CPC ............ *A61F 2/442* (2013.01); *A61B 17/7059* (2013.01); *A61B 17/86* (2013.01); *A61F 2/30767* (2013.01); *A61F 2/30771* (2013.01); *A61F 2/4455* (2013.01); *A61F 2002/2835* (2013.01);

(Continued)

(58) Field of Classification Search
  CPC ............ A61F 2310/00023; A61F 2002/30571; A61F 2002/30784; A61F 2002/30616; A61F 2002/30879; A61F 2002/30578; A61F 2002/2835; A61F 2002/30892; A61F 2002/30018; A61F 2250/0029; A61F 17/86; A61F 17/7059; A61F 2/442; A61F 2/30767; A61F 2/30771; A61F 2/4455
  USPC ......... 606/246–249; 623/17.11, 17.13, 17.15, 623/17.16
  See application file for complete search history.

(56) References Cited

U.S. PATENT DOCUMENTS 5,645,599 A * 7/1997 Samani ...................... 623/17.16
5,749,916 A    5/1998 Richelsoph (Continued)

OTHER PUBLICATIONS

European Office Action for Appl. No. 03 725 283 dated Apr. 2, 2014.

*Primary Examiner* — Pedro Philogene
*Assistant Examiner* — David Comstock
(74) *Attorney, Agent, or Firm* — MH2 Technology Law Group, LLP

(57) ABSTRACT

The implant includes two side walls resting against the vertebral end-plates and an intermediate wall joining the supporting walls. The implant can be deformed for insertion between the vertebrae to be treated to restore the attenuated mobility of the vertebrae, and includes mounting elements mounting on the vertebrae. The side walls have a curved shape, whose convexity is oriented towards the outside of the implant; the intermediate wall has a curved shape, whose convexity is oriented towards the outside of the implant such that it does not form any pronounced angles with the supporting side walls. The supporting side walls and the intermediate wall, have a partially oval shape; and the mounting elements are configured such that the implant can be mounted on the vertebrae.

12 Claims, 1 Drawing Sheet

(52) U.S. Cl.
CPC ............... *A61F2002/30018* (2013.01); *A61F 2002/30571* (2013.01); *A61F 2002/30578* (2013.01); *A61F 2002/30616* (2013.01); *A61F 2002/30784* (2013.01); *A61F 2002/30879* (2013.01); *A61F 2002/30892* (2013.01); *A61F 2250/0029* (2013.01); *A61F 2310/00023* (2013.01)

(56) References Cited

U.S. PATENT DOCUMENTS

| 6,610,093 | B1* | 8/2003 | Pisharodi | 623/17.15 |
| 7,867,276 | B2* | 1/2011 | Matge et al. | 623/17.11 |
| 2008/0262617 | A1* | 10/2008 | Froehlich et al. | 623/14.12 |
| 2009/0118833 | A1* | 5/2009 | Hudgins et al. | 623/17.16 |

* cited by examiner

DYNAMIC INTERVERTEBRAL IMPLANT

CROSS REFERENCE TO RELATED APPLICATIONS

This is a continuation application of U.S. patent application Ser. No. 10/506,219 filed on Sep. 1, 2004, and entitled "DYNAMIC INTERVERTEBRAL IMPLANT" which is a national phase under 35 U.S.C. §371 of International Patent Application No. PCT/FR2003/000799, filed on Mar. 13, 2003, and claims the benefit of French Patent Application No. FR 02/03252, filed on Mar. 15, 2002, all of which are herein incorporated by reference in their entirety. The International Application was published as International Publication No. WO 2003/077806 A1 on Sep. 25, 2003.

FIELD

The present invention relates to an intervertebral implant, notably intended for the treatment of cervical vertebrae by anterior approach route.

BACKGROUND

It is known to use intervertebral implants to restore the anatomic intervertebral space between two vertebrae. However, the existing implants are not completely satisfactory, in particular as regards the treatment of cervical vertebrae by anterior approach route, either because they do not restore perfectly the intervertebral space, or because they form obstacles to the movements of the vertebrae, or because they induce risks of insertion in the vertebral plates, or because they are difficult to implant, or because their durability or the anchoring thereof is questionable.

The document U.S. Pat. No. 5,749,916 describes a fusion cage slit laterally to enable the application of stresses on a graft contained in the wedge and/or for restoring anatomic mobility between two vertebrae.

This implant is not intended for treating cervical vertebrae by anterior approach route, and the implant according to the invention does not comprise any lateral slot.

There is also provided, by the document WO 01/62190, an intervertebral implant comprising a U-shaped body seen laterally, i.e. showing two lateral branches resting against the vertebral plates and a posterior "wall". This body is deformable elastically for the insertion thereof between the vertebrae to be treated and to enable restoration of the mobility of the vertebrae, and forms protruding tabs for the attachment thereof to the vertebrae.

This implant is estimated as not satisfactory from the point of view of the restoration of an intervertebral space with mobility of the vertebrae. Indeed, the screw attachment of this implant is considered as not suitable for such a restoration, taking into account the risks induced of a vertebral fusion by growth of the bony cells, which may result in immobilisation of the vertebrae. Moreover, the resistance of this implant to the repeated stresses transmitted by these vertebrae is considered as questionable.

The purpose of the present invention is to remedy these shortcomings.

SUMMARY

Its main object consists thus in providing an intervertebral implant capable of restoring adequate anatomic space between two vertebrae while keeping, in all certainty over time, the relative mobility of the two vertebrae treated.

Another object of the invention is to provide an intervertebral implant offering perfect resistance to the repeated stresses transmitted by these vertebrae.

The implant in question comprises, as known, two lateral walls bearing against the vertebral plates and an intermediate wall for connection of these lateral bearing walls, this implant being deformable elastically for the insertion thereof between the vertebrae to be treated and to enable restoration of dampened mobility of these vertebrae, and including means for the assembly thereof to these vertebrae.

According to the invention,
- said lateral bearing walls show, seen laterally, curved shapes with their convexity turned to the outside of the implant;
- said intermediate wall shows a curved shape, with its convexity turned to the outside of the implant, and is such that it does not form any marked angles with said lateral bearing walls, these lateral bearing walls and this intermediate wall having thus, seen laterally, partial oval "water drop"-like shape; and
- the means for fastening the implant to the vertebrae are designed to enable non rigid assembly of this implant to these vertebrae, i.e. authorising slight deformation of the implant with respect to the vertebrae as the latter are moving.

The curved shaped of said lateral walls enables these walls to adapt accurately to the shape of the respective faces of the vertebral plates, thereby ensuring certain retention of the implant between the vertebrae.

Once in place, the implant does not oppose the movements of the vertebrae because of the deformability of the intermediate wall thereof; the risk of inserting the implant in the vertebral plates is consequently vastly reduced, if not eliminated, the more so because said lateral walls possess wide contact surfaces with the vertebral plates.

The absence of marked angles between said lateral bearing walls and said intermediate wall enables to avoid, on the body of the implant, any concentration of the loads transmitted by the vertebrae at a given location of this body, and enables consequently to this implant to have perfect resistance to these loads over time.

The shape aforementioned of the body of the implant enables besides certain deformation of the implant with respect to the vertebrae when the latter are moving, this deformation being not prevented by said means for fastening this implant to the vertebrae and being only limited by the latter.

This mobility prevents any risks of fusion of the intervertebral space further to bony cells growing around the implant, and therefore to keep total mobility of the vertebrae relative to one another over time.

Preferably, said intermediate wall is so shaped as, when not deformed, to maintain said lateral bearing walls at a distance from one another which is slightly greater than the height of the intervertebral space to be restored.

This intermediate wall is therefore slightly constrained when the implant is placed and enables to ensure, by elastic return, slight support of the upper vertebra relative to the lower vertebra.

Advantageously, the implant is made simply by folding a single piece of appropriate material, notably a sheet metal flank. The material used may be, notably, titanium, aluminium and vanadium alloy, known as "TA6V".

According to a preferred embodiment of the invention, said attachment means of the implant to the vertebrae comprise at least one series of ribs parallel to one another, with sharp free ridges, protruding from the external face of the free end of a lateral bearing wall.

These ribs are intended for insertion in the anterior zone of the body of the adjacent vertebra.

The implant may comprise two series of ribs, the one on one of the lateral bearing walls, the other on the other lateral bearing wall. For treating cervical vertebrae, the implant exhibits advantageously a "lower" lateral bearing wall, i.e. bearing against the lower vertebra during placement, with a length greater than that of the other lateral bearing wall.

The implant described above may be part of a set of implants including at least one other intervertebral implant, intended to realise a fusion between the two vertebrae to be treated; this other implant, so-called "fusion" implant, has a structure similar to that of the implant described above, but comprises attachment means which enable the rigid assembly thereof to the vertebrae treated.

Preferably, in such a case, said means enabling to attach the "fusion" implant comprise at least one tab integral with one of said lateral bearing walls, drilled with a reception hole of an anchoring screw, this screw being intended for insertion in the body of the corresponding vertebra.

Said lateral bearing walls of the "fusion" implant may exhibit surface coverings promoting their osteo-integration and/or comprise holes which communicate the space delineated between them, with the exterior of the implant. A bony graft may then be placed in this space.

For better understanding thereof, the invention is again described below with reference to the appended schematic drawing, representing for non limiting exemplification purposes, a possible embodiment possible of the intervertebral implant in question, and a "fusion" implant included in a set of implants also affected, said set comprising said intervertebral implant according to the invention and said "fusion" implant.

BRIEF DESCRIPTION OF THE DRAWINGS

FIGS. 1 and 2 represent an intervertebral implant 1 for the treatment of cervical vertebrae 10 by anterior approach route.

DESCRIPTION OF THE EMBODIMENTS

Figure 1:
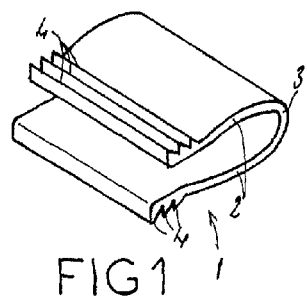
FIG. 1 is a perspective view of the intervertebral implant in question.
Figure 2:
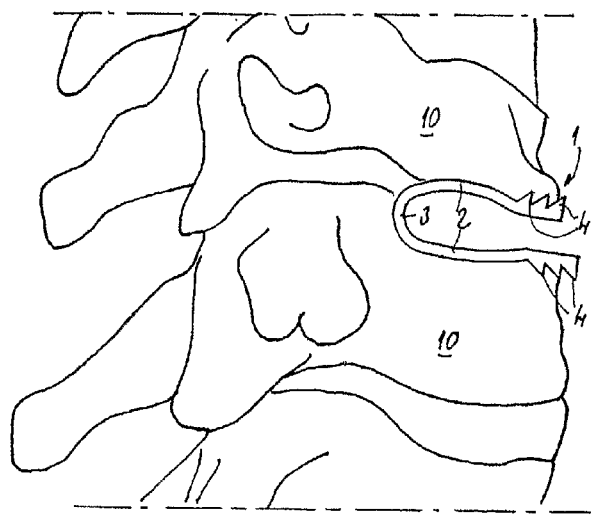
FIG. 2 is a side view thereof after placement thereof.

As it appears, the implant 1 is realised by folding a given piece of material and exhibits, seen laterally, i.e. in the sagittal plane after implantation, a curved shape delineating two lateral bearing walls 2 and one intermediate wall 3.

Said piece of material is a sheet flank made of titanium, aluminium and of vanadium alloy known as "TA6V".

The lateral walls 2 show, seen laterally, domed shapes on the greatest portion of their length, the convexities thereof being turned towards the exterior of the implant 1. At their free end zones, these lateral bearing walls 2 are rectilinear in shape and comprise each a series of ribs 4.

The length of the "lower" wall 2, i.e. abutting the lower vertebra during implantation, is greater than that of the other wall 2.

The intermediate wall 3 has a curved shape whereof the convexity is turned towards the exterior of the implant. As appears clearly, it does not form any marked angles with the lateral bearing walls 2, these lateral bearing walls 2 and this intermediate wall 3 having thus, seen laterally, partially oval "water drop"-like shape.

The intermediate wall 3 is moreover deformable elastically between a neutral form, wherein it maintains normally the walls 2 at a distance from one another which is slightly greater than the height of the intervertebral space to be restored, and a constrained shape, wherein said wall 3 enables to bring the free ends of both walls 2 together. This bringing together is such that it enables to reduce the height of the implant 1 so that such height is smaller than the height of the intervertebral space to be restored.

The ribs 4 are parallel to one another and protrude from the free end zone of each wall 2, towards the exterior of the implant 1. Each of them is delineated by an anterior face perpendicular to the longitudinal direction of the implant 1 and by a tilted posterior face, forming an angle of approximately 500 with the anterior face. These ribs 4 thus exhibit relatively sharp free ridges.

The implant 1 represented for exemplification purposes exhibits the following dimensions:
maximum dimension of the implant in the sagittal plane: approximately 17 mm;
difference in length of the walls 2: approximately 1 mm;
dimension of the implant in the front plane: approximately 18 mm;
thickness of said flank at the walls 2 and of the wall 3: approximately 1 mm;
maximum thickness of the implant 1, at the exterior domed faces of the lateral walls 2: approximately 7 mm;
curvature radius of the upper half of the intermediate wall 3: approximately 2.7 mm;
curvature radius of the lower half of the intermediate wall 3: approximately 3.3 mm;
curvature radius of the domed zone of the upper lateral wall 2: 10 mm;
curvature radius of the domed zone of the lower lateral wall 2: approximately 25 mm.

In practice, the walls 2 are brought towards one another by deformation of the wall 3, to enable insertion of the implant 1 between the vertebral plates of the two vertebrae 10 to be treated, then, once said insertion is completed, the walls 2 are released, which presses said walls against these vertebral plates. The ribs 4 are inserted in the vertebral plates and enable non rigid assembly of the implant 1 to these vertebrae or tissues, i.e. allowing slight deformation of the implant with respect to the vertebrae as the vertebrae are moving, while opposing any expulsion of the implant.

The domed shape of the walls 2 enables these walls to match precisely the shape exhibited by the respective faces of these vertebral plates, and ensures certain retention of the implant between the vertebrae 10. The elastic stress remaining in the wall 3 enables to maintain the ribs 4 inserted in the vertebrae 10.

Figure 3:
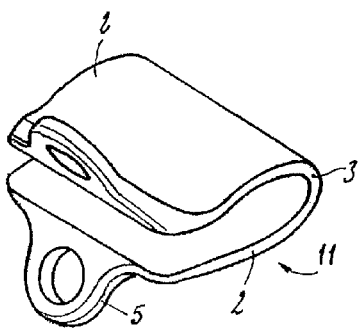
FIG. 3 is a perspective view of said "fusion" implant.
Figure 4:
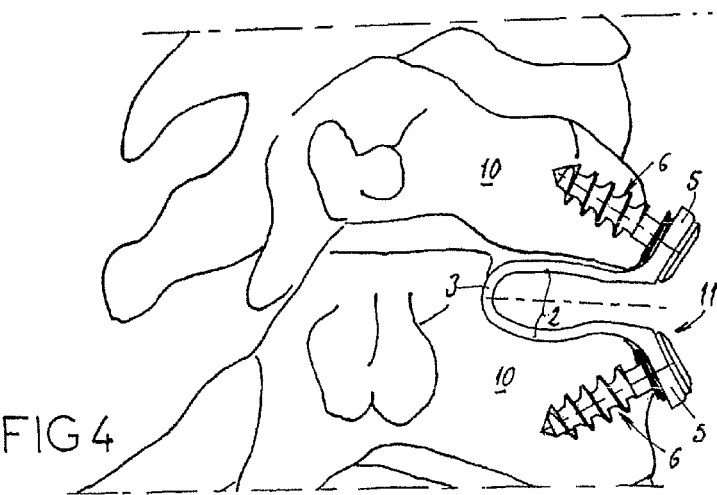
FIG. 4 is a side view of this "fusion" implant after placement.

The "fusion" implant 11 shown on FIGS. 3 and 4 have a structure similar to that of the implant 1 described above, except that the walls 2 comprise two tabs 5, interconnected therewith and extend their free ends.

Each of these tabs 5 is attached to the end of the wall 2 which supports the latter by two curved lateral connection zones, which enable to ensure perfectly solid link of this tab 5 and of the wall 2, and is drilled with a hole accommodating an anchoring screw 6. This screw 6 is intended to be inserted in the body of the corresponding vertebra 10, as shown on FIG. 4.

Each tab 5 forms an angle of the order of 120.degree. with the general antero-posterior direction of the wall 2 to which said tab is attached, and exhibits a thickness greater than that of the remainder of the implant 1. This thickness is approximately 1.5 mm in the example represented.

The "fusion" implant 11 is used to realise a fusion between the two vertebrae 10 to be treated.

It appears from the foregoing that the invention brings a decisive improvement to the anterior technique, by providing an intervertebral implant enabling perfect restoration of the intervertebral space, without opposing the movements of the vertebrae, without inducing any risks of insertion in the vertebral plates nor of risk of fusion by growing bony cells, while being easy to be implanted and whereof the durability is not questionable.

It goes without saying that the invention is not limited to the embodiment described above for exemplification purposes, but it includes conversely all the embodiment variations covered by the appended claims.

What is claimed is:

1. An intervertebral cervical implant for treating cervical vertebrae, comprising:
    a first bearing wall having a domed surface along its length with a convexity towards the exterior of the implant for matching a shape and bearing against a face of a vertebral endplate of one of the cervical vertebrae;
    a second bearing wall having a domed surface along its length with a convexity towards the exterior of the implant for matching a shape and bearing against a face of an adjacent vertebral endplate of another of the cervical vertebrae; and
    an intermediate wall connecting the first bearing wall to the second bearing wall such that the first and second bearing walls are substantially parallel to one another and are spaced apart from one another, the first and second bearing walls each having a first end connected to the intermediate wall and a free end distant from the intermediate wall, the intervertebral cervical implant being capable of deformation for insertion between the cervical vertebrae;
    wherein at least one of the first and second bearing walls includes a series of vertebral engaging protrusions extending lengthwise completely across a width of either the first bearing wall or the second bearing wall, the vertebral engaging protrusions being parallel to one another and protruding from the outer convex surface for securing the implant to the cervical vertebrae.

2. The implant of claim 1, wherein the intermediate wall is C-shaped.

3. The implant of claim 1, wherein the intermediate wall has a continuous, curved shape without marked angles.

4. The implant of claim 1, wherein the outer convex surface of the first bearing wall includes a radius of curvature that is less than a radius of curvature of the outer convex surface of the second bearing wall.

5. The implant of claim 1, wherein the length of the first bearing wall is less than the length of the second bearing wall, the lengths being measured from the intermediate wall to the free ends of the first and second bearing walls.

6. The implant of claim 1, wherein the vertebral engaging protrusions are disposed proximate a free end of a respective one of the first and second bearing walls.

7. The implant of claim 1, wherein the vertebral engaging protrusions do not extend beyond the respective free ends of the first and second bearing walls.

8. The implant of claim 1, wherein each of the vertebral engaging protrusions includes a sharp rib.

9. The implant of claim 1, wherein each of the vertebral engaging protrusions includes an elongated rib.

10. The implant of claim 1, further including an outer surface modification configured to promote bony ingrowth.

11. The implant of claim 10, wherein the outer surface modification include a plurality of holes in at least one of the first and second bearing walls.

12. The implant of claim 1, wherein the implant has a first width proximate the intermediate wall and a second width proximate the free ends of the first and second bearing wall, wherein the first width is greater than the second width.

\* \* \* \* \*